US012667240B2

(12) United States Patent
Morimoto et al.

(10) Patent No.: US 12,667,240 B2
(45) Date of Patent: *Jun. 30, 2026

(54) ENDOSCOPE

(71) Applicant: FUJIFILM Corporation, Tokyo (JP)

(72) Inventors: Yasuhiko Morimoto, Kanagawa (JP); Satoru Okada, Kanagawa (JP); Tsuneo Fukuzawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/644,034

(22) Filed: Apr. 23, 2024

(65) Prior Publication Data

US 2024/0268632 A1 Aug. 15, 2024

Related U.S. Application Data

(63) Continuation of application No. 17/947,187, filed on Sep. 19, 2022, now Pat. No. 11,998,170, which is a
(Continued)

(30) Foreign Application Priority Data

Mar. 7, 2019 (JP) ................................. 2019-041825

(51) Int. Cl.
*A61B 1/00* (2006.01)
*A61B 1/018* (2006.01)

(52) U.S. Cl.
CPC ...... *A61B 1/00098* (2013.01); *A61B 1/00087* (2013.01); *A61B 1/018* (2013.01)

(58) Field of Classification Search
CPC .. A61B 1/00098; A61B 1/00087; A61B 1/018
See application file for complete search history.

(56) References Cited

U.S. PATENT DOCUMENTS 4,841,949 A * 6/1989 Shimizu ................. A61B 1/015
600/107
5,569,157 A * 10/1996 Nakazawa ......... A61B 1/00098
600/106
(Continued)

FOREIGN PATENT DOCUMENTS

CN 106913359 7/2017
CN 108542336 9/2018
(Continued)

OTHER PUBLICATIONS

"Office Action of U.S. Appl. No. 17/398,558", issued on Feb. 2, 2024, pp. 1-17.
(Continued)

*Primary Examiner* — Timothy J Neal
(74) *Attorney, Agent, or Firm* — JCIPRNET

(57) ABSTRACT

An endoscope including an insertion unit, a treatment tool insertion channel, a treatment tool outlet, an elevator, and a plurality of wall is provided. The insertion unit has a soft part, a bendable part, and a distal end part arranged in order from a proximal end side toward a distal end side in a direction of a longitudinal axis. The treatment tool insertion channel is inserted into the insertion unit. The treatment tool outlet is connected to a distal end of the treatment tool insertion channel. The elevator is rotatable about a rotating shaft between a standing position and a fallen position, and includes a guide surface guiding a treatment tool led out of the treatment tool outlet. The plurality of walls encloses a space in which the elevator is housed, wherein a first wall, which is opposite to the guide surface in a case where the elevator is in the standing position, among the plurality of walls is made of a material harder than at least a second wall among the plurality of walls.

17 Claims, 9 Drawing Sheets

Related U.S. Application Data continuation of application No. 16/808,407, filed on Mar. 4, 2020, now Pat. No. 11,484,188.

(56) References Cited

U.S. PATENT DOCUMENTS

| | | | | |
|---|---|---|---|---|
| 5,662,588 | A * | 9/1997 | Iida | A61B 1/00091 |
| | | | | 600/125 |
| 6,251,085 | B1 * | 6/2001 | Tezuka | A61M 25/09 |
| | | | | 604/524 |
| 10,485,411 | B2 | 11/2019 | Morimoto | |
| 10,806,338 | B2 | 10/2020 | Morimoto et al. | |
| 11,484,188 | B2 * | 11/2022 | Morimoto | A61B 1/00098 |
| 11,998,170 | B2 * | 6/2024 | Morimoto | A61B 1/00098 |
| 2002/0091303 | A1 | 7/2002 | Ootawara et al. | |
| 2004/0049095 | A1 * | 3/2004 | Goto | A61B 1/00098 |
| | | | | 600/107 |
| 2007/0197871 | A1 | 8/2007 | Geitz et al. | |
| 2007/0249940 | A1 * | 10/2007 | Kohno | A61B 1/00098 |
| | | | | 600/463 |
| 2009/0079821 | A1 | 3/2009 | Bousquet et al. | |
| 2015/0173711 | A1 | 6/2015 | Hiraoka | |
| 2017/0112362 | A1 | 4/2017 | Morimoto | |
| 2017/0127920 | A1 | 5/2017 | Morimoto | |
| 2018/0249895 | A1 | 9/2018 | Calabrese et al. | |
| 2019/0059702 | A1 | 2/2019 | Hosogoe | |
| 2019/0239726 | A1 | 8/2019 | Hiraoka | |
| 2020/0390322 | A1 | 12/2020 | Saito | |
| 2021/0113065 | A1 | 4/2021 | Hosogoe | |
| 2021/0113066 | A1 | 4/2021 | Hosogoe | |
| 2021/0113067 | A1 | 4/2021 | Hosogoe | |
| 2021/0290042 | A1 | 9/2021 | Hosogoe | |

FOREIGN PATENT DOCUMENTS

| | | | | | |
|---|---|---|---|---|---|
| CN | 108685556 | | 10/2018 | | |
| EP | 1857039 | | 11/2007 | | |
| EP | 3165149 | | 2/2018 | | |
| JP | 3188206 | | 7/2001 | | |
| JP | 2003305002 | | 10/2003 | | |
| JP | 2004261360 | | 9/2004 | | |
| JP | 2007307086 | | 11/2007 | | |
| JP | 2011136193 | | 7/2011 | | |
| JP | 2012070792 | * | 4/2012 | ......... | A61B 1/00098 |
| JP | 2017079876 | | 5/2017 | | |
| JP | 2017086399 | | 5/2017 | | |
| JP | 6223723 | | 11/2017 | | |
| JP | 2018171255 | | 11/2018 | | |
| JP | 2019030645 | | 2/2019 | | |
| WO | 2018070525 | | 4/2018 | | |
| WO | 2018079790 | | 5/2018 | | |
| WO | 2019131836 | | 7/2019 | | |

OTHER PUBLICATIONS

"Office Action of China Related Application No. 202080018732.7", issued on Oct. 28, 2022, with English translation thereof, p. 1-p. 9.

"International Search Report (Form PCT/ISA/210) of PCT/JP2020/009683", mailed on Apr. 21, 2020, with English translation thereof, pp. 1-5.

"International Preliminary Report on Patentability (Form PCT/IPEA/409) of PCT/JP2020/009683," completed on Aug. 11, 2020, with English translation thereof, pp. 1-7.

"Office Action of Co-pending U.S. Appl. No. 17/398,558", issued on Aug. 2, 2024, pp. 1-16.

"Office Action of U.S. Related Application, U.S. Appl. No. 17/398,558", issued on Dec. 19, 2024, p. 1-p. 15.

"Office Action of China Counterpart Application", issued on Dec. 11, 2024, with English translation thereof, p. 1-p. 17.

"Office Action of U.S. Related Application, U.S. Appl. No. 17/398,558", issued on Jun. 13, 2025, p. 1-p. 20.

"Office Action of Japan Related Application, Application No. 2019-041825", issued on Sep. 17, 2021, with English translation thereof, p. 1-p. 8.

"Office Action of Japan Related Application, Application No. 2019-041825", issued on Jan. 7, 2022, with English translation thereof, p. 1-p. 6.

"Office Action of U.S. Related Application, U.S. Appl. No. 16/808,407", issued on Nov. 29, 2021, p. 1-p. 18.

"Office Action of U.S. Related Application, U.S. Appl. No. 16/808,407", issued on Apr. 6, 2022, p. 1-p. 16.

"Office Action of Japan Related Application, Application No. 2022-039201", issued on Nov. 9, 2022, with English translation thereof, p. 1-p. 10.

"Office Action of China Counterpart Application", issued on May 21, 2025, with English translation thereof, pp. 1-14.

* cited by examiner

FIG.7

ENDOSCOPE

CROSS-REFERENCE TO RELATED APPLICATIONS

This application is a continuation application of and claims the priority benefit of U.S. application Ser. No. 17/947,187, filed on Sep. 19, 2022. The prior U.S. application Ser. No. 17/947,187 is a continuation application of and claims the priority benefit of U.S. application Ser. No. 16/808,407, filed on Mar. 4, 2020. The prior U.S. application Ser. No. 16/808,407 claims priority under 35 U.S.C. § 119 to Japanese Patent Application No. 2019-041825, filed on Mar. 7, 2019. The above application is hereby expressly incorporated by reference, in its entirety, into the present application.

BACKGROUND OF THE INVENTION

1. Field of the Invention

The present invention relates to an endoscope, and more particularly, to an endoscope comprising an elevator making a treatment tool, which is led out of an opening portion, stand.

2. Description of the Related Art

An endoscope, which comprises an elevator and an elevator-housing space provided in a distal-end-part body of an insertion unit to be inserted into a body cavity, is known in the related art. A treatment tool-insertion channel is inserted into the insertion unit, a treatment tool led out of an opening portion of the elevator-housing space is made to stand by the elevator, and the lead-out direction of the treatment tool can be adjusted by a change in the standing angle of the elevator.

For example, JP2017-086399A discloses an endoscope that comprises a projection portion provided on a fixing sleeve for fixing a connecting pipe to a treatment tool-insertion tube to smoothly advance the treatment tool toward the connecting pipe from the treatment tool-insertion tube in an up-angle form. WO2018/079790A discloses an endoscope where a second guide groove having an opening width smaller than a treatment tool-insertion hole is formed on the inner surface of the treatment tool-insertion hole to suppress the wobble of treatment tools having different cross-sectional diameters. Further, JP6223723B discloses an ultrasound endoscope where a notch through which a flexible wire-like treatment tool passes is formed on the anterior wall of an elevator-storage recess to increase the degree of freedom in the protruding direction of the flexible wire-like treatment tool.

SUMMARY OF THE INVENTION

An endoscope is used together with various treatment tools, such as a puncture needle, a guide wire, and a stent. For example, a treatment method of discharging substance present in a cyst into the alimentary canal by puncturing a cyst with a puncture needle, inserting a guide wire into the cyst, and putting a stent in a guide wire serving as a guide has been widely spread.

However, in a case where a treatment tool (puncture needle) is to be taken out using the guide wire as a guide, the guide wire is also moved together with the puncture needle and is frequently taken out of the cyst. In a case where the guide wire is taken out, the stent cannot be put at a desired position using the guide wire as a guide after the puncture needle is taken out. Further, a manipulation for a long time is caused in a case where a guide wire is installed again.

Furthermore, a guide wire is sandwiched by the elevator and the distal-end-part body to increase the sliding resistance of the guide wire and to inhibit the guide wire from being taken out of a position where puncturing is performed. The endoscope includes an electrical cable that is provided in the distal-end-part body and is to be connected to an observation optical system. Further, the ultrasound endoscope includes an ultrasound vibrator mounted on the distal end part, and the ultrasound vibrator is driven with a high voltage of about 50 V. For this reason, the distal-end-part body is generally formed of a resin member in terms of electrical safety.

On the other hand, since there is a treatment tool that is formed of a metal tube, such as stainless steel, like a puncture needle, the bending stiffness of the treatment tool may be high. Accordingly, a large standing force is required to make the treatment tool stand by an elevator. As a standing force (a force for bending the puncture needle by the elevator) is larger, the puncture angle of the puncture needle can be further increased and puncturing can be performed in a wide range. However, in a case where a standing force is increased, the puncture needle is pressed against a resin portion of the distal end part opposite to the elevator and is damaged. For this reason, there is a problem that a standing force cannot be increased.

The invention has been in consideration of the above-mentioned circumstances, and an object of the invention is to provide an endoscope that can prevent the scrape of a distal-end-part body caused by a treatment tool, such as a puncture needle and a guide wire, and suppress degradation over time.

To achieve the object of the invention, an endoscope according to an aspect of the invention comprises a distal-end-part body that is provided at a distal end of an insertion unit extending in a direction of a longitudinal axis; the distal-end-part body includes an elevator-housing space-forming wall that forms an elevator-housing space opened in a direction perpendicular to the direction of the longitudinal axis, a lead-out portion that forms a distal end of a treatment tool-insertion channel inserted into and disposed in the insertion unit and includes a treatment tool outlet opened into the elevator-housing space, and an elevator that is provided in the elevator-housing space so as to be rotatable about a rotating shaft between a standing position and a fallen position and includes a guide surface guiding a treatment tool led out of the treatment tool outlet; the elevator-housing space-forming wall includes an opening wall portion provided on an opening side of the elevator-housing space; and an opposite wall portion, which is opposite to the guide surface in a case where the elevator is in the standing position, of the opening wall portion is made of a material harder than the other wall portion other than the opposite wall portion.

According to the endoscope of the aspect of the invention, the opposite wall portion, which is opposite to the guide surface of the elevator, of the opening wall portion of the elevator-housing space-forming wall is made of a material harder than the other wall portion other than the opposite wall portion. Accordingly, even though a treatment tool is sandwiched by the elevator and the opposite wall portion, it is possible to prevent the distal-end-part body from being scraped off. Therefore, the degradation of the endoscope over time can be prevented.

BRIEF DESCRIPTION OF THE DRAWINGS

FIG. 7 is a side cross-sectional view showing a state where a guide wire is fixed.

DESCRIPTION OF THE PREFERRED EMBODIMENTS

Endoscopes according to embodiments of the invention will be described below with reference to the accompanying drawings.

Endoscope

Figure 1:
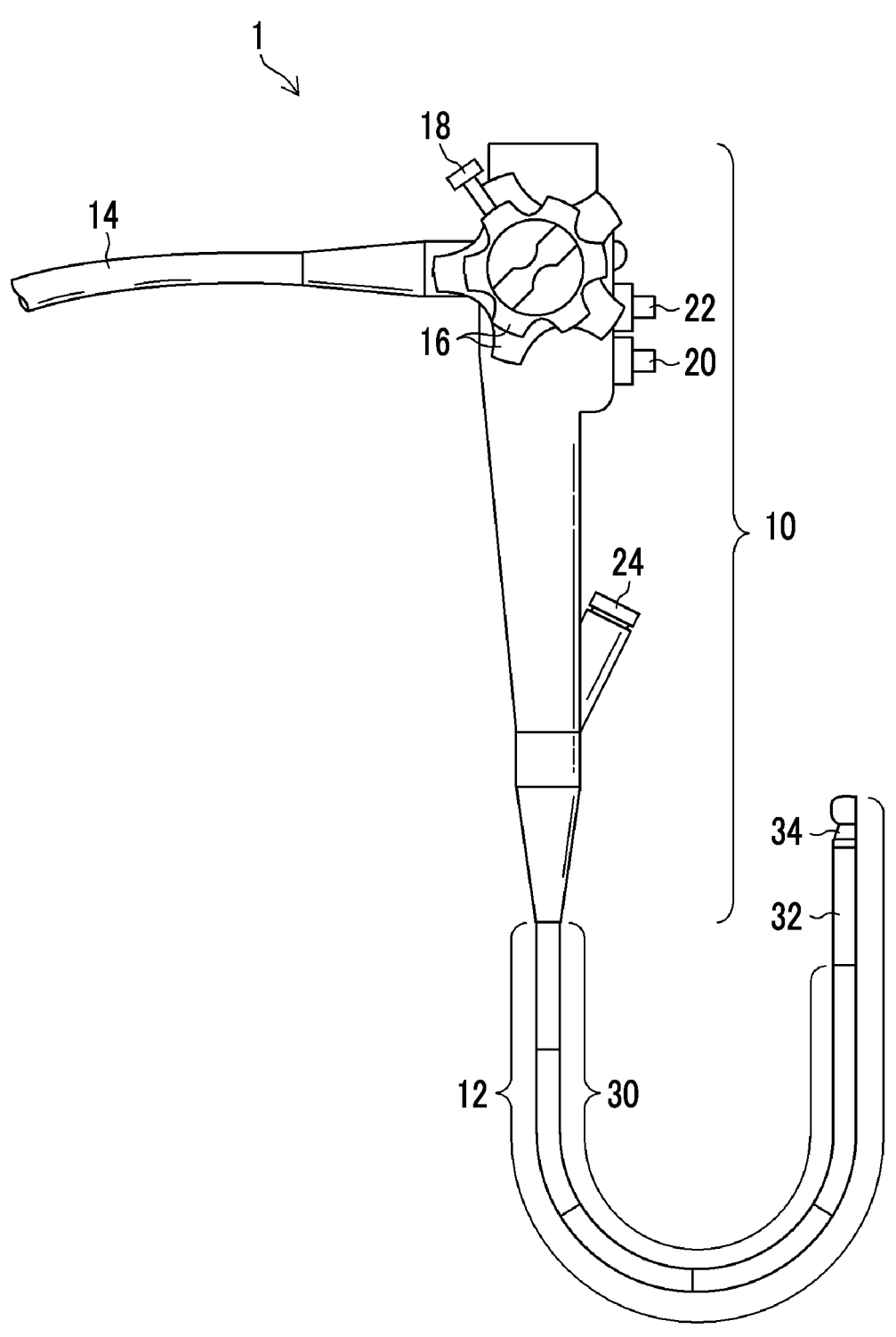
FIG. 1 is a diagram showing the entire ultrasound endoscope according to an embodiment of the invention.

FIG. 1 is a diagram showing the entire endoscope 1 to which the invention is applied. Embodiments to be described below will be described using an ultrasound endoscope as an example, but the invention can also be applied to an endoscope other than an ultrasound endoscope. That is, as long as an endoscope includes an elevator and an opening out of which a treatment tool is to be led, the invention can be applied to the endoscope.

The endoscope 1 shown in FIG. 1 includes an operation unit 10 that allows an operator to perform various operations in a state in which the operator grips the operation unit 10, an insertion unit 12 that is to be inserted into a patient's body cavity, and a universal cord 14. The endoscope 1 is connected to system component devices of an endoscope system, such as a processor device and a light source device, through the universal cord 14.

The operation unit 10 is provided with various operation members that are to be operated by an operator, and is provided with, for example, angle knobs 16, a standing operation lever 18, an air/water supply button 20, a suction button 22, and the like.

Further, the operation unit 10 is provided with a treatment tool inlet 24 through which a treatment tool is to be inserted into a treatment tool-insertion channel inserted into the insertion unit 12.

The insertion unit 12 extends from the distal end of the operation unit 10, and the entire insertion unit 12 is formed in an elongated shape so as to have a small diameter.

Further, the insertion unit 12 includes a soft part 30, a bendable part 32, and a distal end part 34 that are arranged in this order from the proximal end side toward the distal end side.

The soft part 30 occupies a large portion of the insertion unit 12 from the proximal end side, and has flexibility to be bent in any direction. In a case where the insertion unit 12 is inserted into a body cavity, the soft part 30 is bent along an insertion path into the body cavity.

Since the bendable part 32 is adapted to be bent in a vertical direction and a horizontal direction by an operation for rotating the angle knobs 16 of the operation unit 10, the distal end part 34 can face in a desired direction in a case where the bendable part 32 is operated to be bent.

The distal end part 34 comprises a distal-end-part body 36 of which the detail will be described later with reference to FIGS. 2 to 4, and an ultrasound transducer 50 including a plurality of ultrasound vibrators is provided on the distal end side of the distal-end-part body 36.

The universal cord 14 shown in FIG. 1 includes an electrical cable, a light guide, and a fluid tube therein. A connector is provided at the end portion (not shown) of the universal cord 14. Accordingly, in a case where the connector is connected to predetermined system component devices of the endoscope system, such as a processor device and a light source device, electric power, control signals, illumination light, liquid, gas, and the like necessary for the operation of the endoscope 1 are supplied to the endoscope 1 from the system component devices and data of an observation image acquired by an image pickup unit and data of an ultrasound image acquired by the ultrasound transducer are transmitted to the system component devices from the endoscope 1. The observation image and the ultrasound image transmitted to the system component devices are displayed on a monitor, so that an operator can observe the observation image and the ultrasound image.

First Embodiment

Configuration of Distal End Part

Subsequently, the configuration of the distal end part 34 of the insertion unit 12 of the endoscope according to the first embodiment will be described. FIG. 2 is a perspective view showing the appearance of the distal end part 34 and is a diagram showing a state where the elevator 60 is in a fallen position. FIG. 3 is a perspective view showing the appearance of the distal end part 34 and is a diagram showing a state where the elevator 60 is in a standing position. FIG. 4 is a side cross-sectional view.

The distal end part 34 includes the distal-end-part body 36 that forms an outer wall of the distal end part 34 and partition walls provided in the distal end part 34, and various components disposed in the distal-end-part body 36 are housed and held in a housing portion provided in the distal-end-part body 36.

Although details are omitted, a part of the distal-end-part body 36 is formed of a separate block so that the distal-end-part body 36 can be attachably and detachably detached. Accordingly, the respective components can be assembled in the predetermined housing portion in a state where the separate block is detached. In a case where the separate block is mounted on the distal-end-part body 36 after the respective components are assembled in the housing portion, the respective components are housed and held in the housing portion and are fixed to the distal end part 34.

The distal-end-part body 36 is made of an insulating material having an insulating property, for example, resin materials (plastics), such as a methacrylic resin, a polyphenylsulfone resin, a polyetherimide resin, a polyether ether ketone resin, and polycarbonate.

Figure 2:
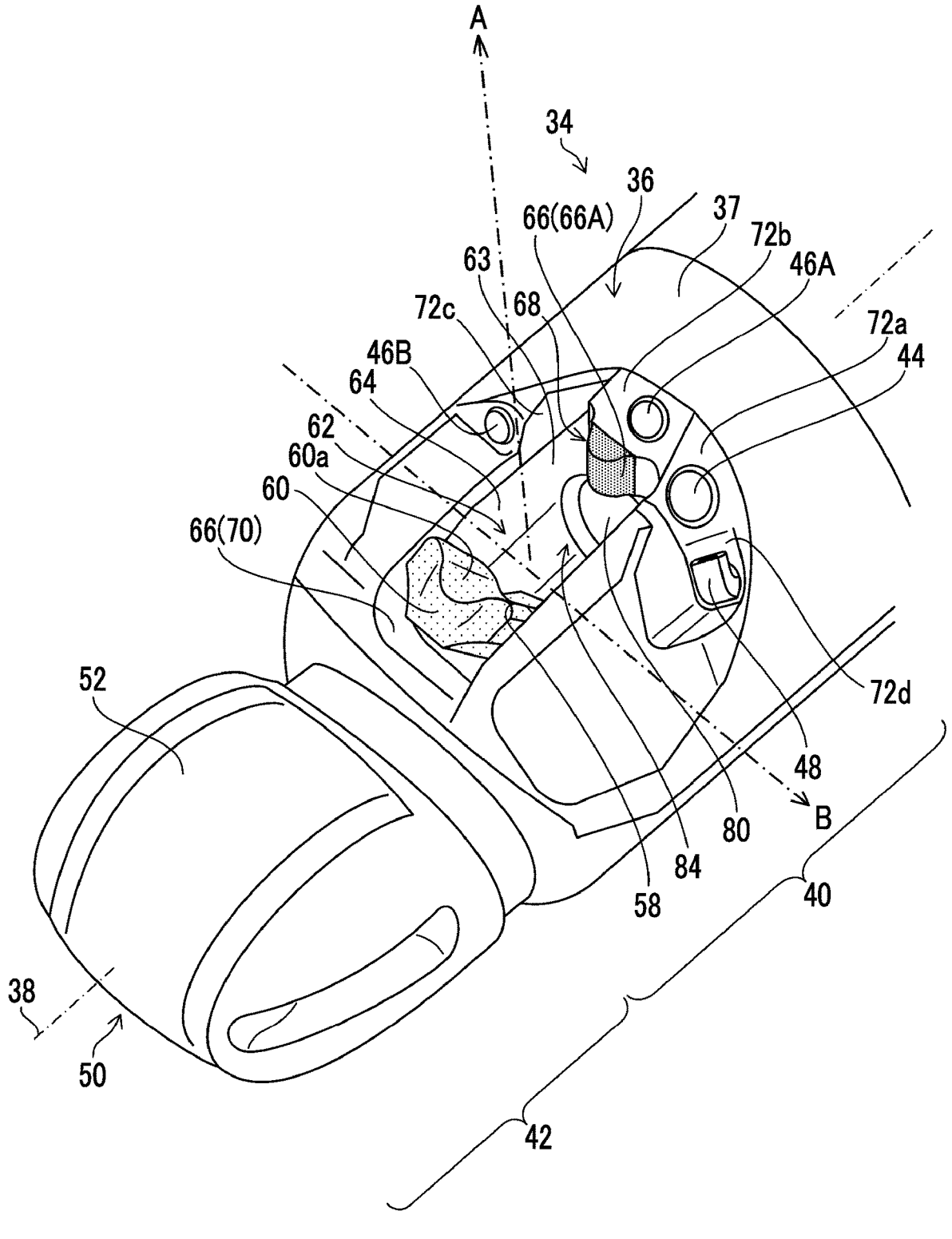
FIG. 2 is a perspective view showing the appearance of a distal end part in a case where an elevator is in a fallen state.
Figure 3:
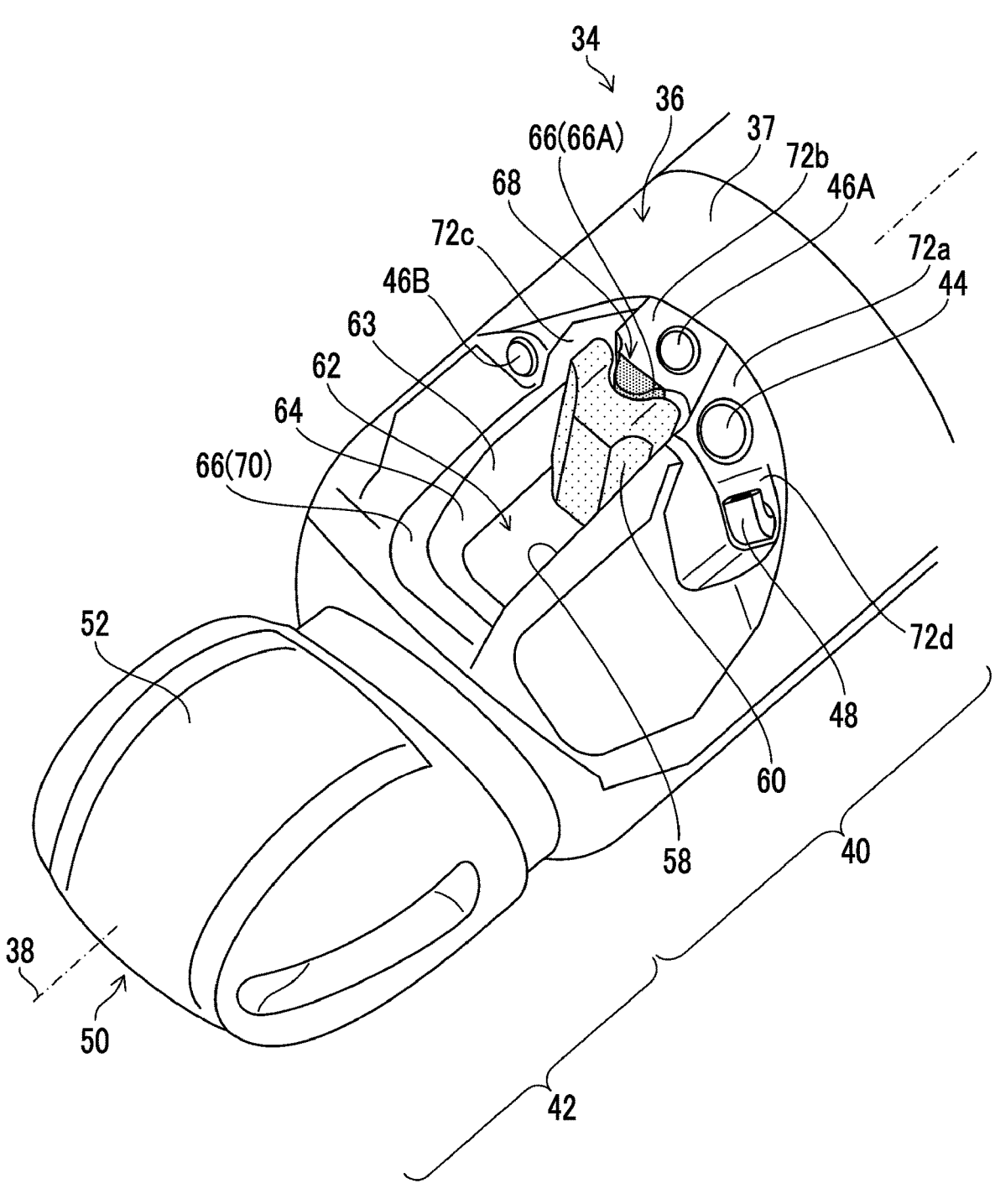
FIG. 3 is a perspective view showing the appearance of the distal end part in a case where the elevator is in a standing state.
Figure 4:
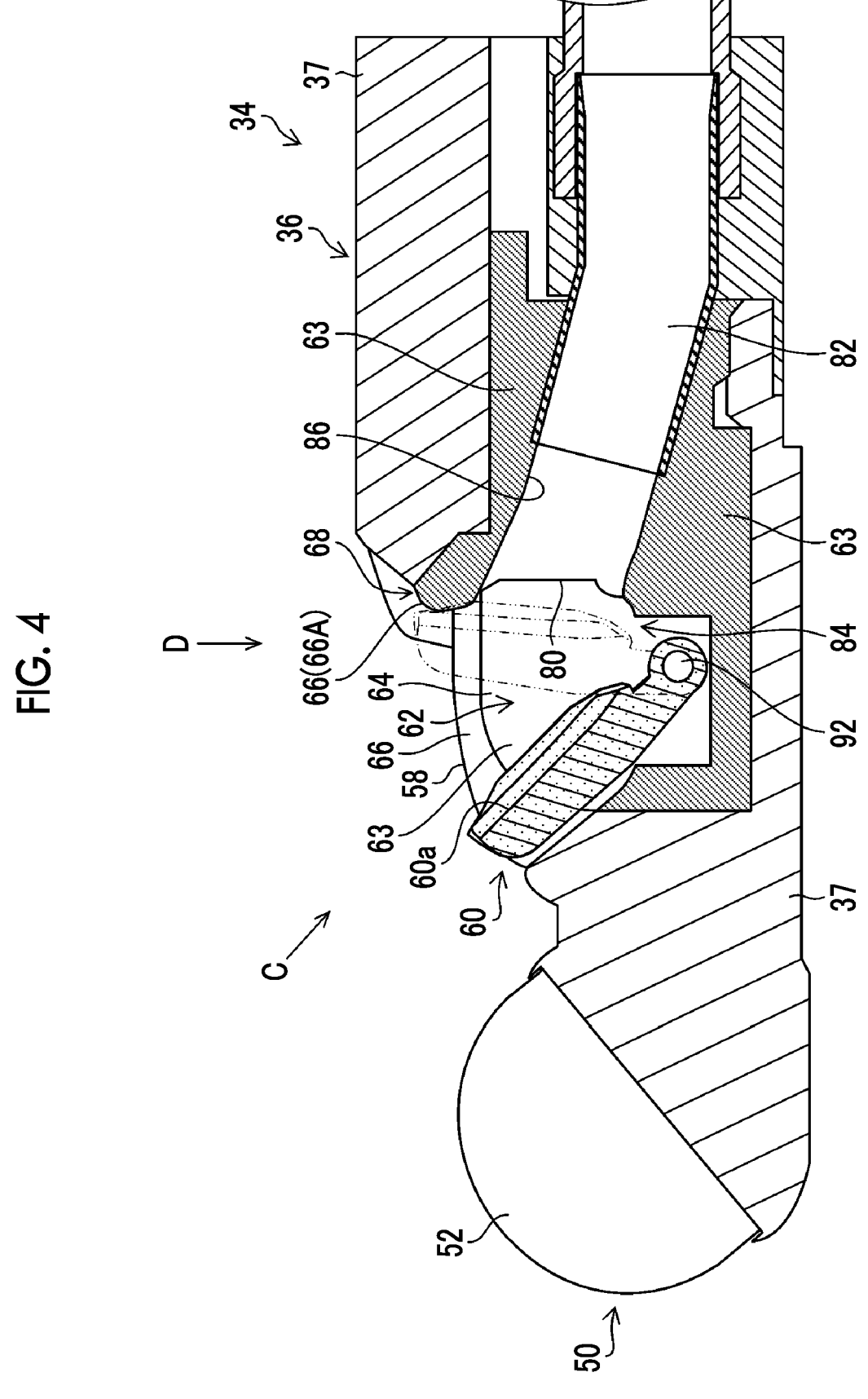
FIG. 4 is a side cross-sectional view of the distal end part.

As shown in FIGS. 2 to 4, the distal-end-part body 36 includes: a base portion 40 that forms an observation optical system, a lead-out portion, an elevator guiding a treatment tool led out of the lead-out portion, and the like; and an extension portion 42 that extends from the base portion 40 toward the distal end side and holds the ultrasound transducer 50.

A convex ultrasound transducer 50 transmitting and receiving ultrasound is disposed on the extension portion 42. The ultrasound transducer 50 includes an ultrasound transmitting/receiving surface 52, and the ultrasound vibrators are arranged in a curved shape in the direction of a longitudinal axis 38 of the insertion unit 12 to form the ultrasound transmitting/receiving surface 52. Data used to generate the ultrasound image of an internal tissue are acquired by the ultrasound transducer 50.

As shown in FIGS. 2 and 3, the distal-end-part body 36 is provided with an observation window 44, a first illumination window 46A, a second illumination window 46B, an air/water supply nozzle 48, and an opening portion 58 out of which a treatment tool is to be led.

The opening portion 58 is provided in the base portion 40 of the distal-end-part body 36, and a treatment tool is led out of the opening portion 58 to a range that is to be scanned with ultrasound by the ultrasound transducer 50. An elevator-housing space 62 is a space of which the periphery is defined by an elevator-housing space-forming wall 64, and the elevator-housing space 62 is opened in a direction perpendicular to the direction of the longitudinal axis 38 of the insertion unit 12, so that the opening portion 58 is formed.

As shown in FIGS. 2 and 4, a lead-out portion 84 including a treatment tool outlet 80, which is opened into the elevator-housing space 62, is disposed on the proximal end side of the elevator-housing space 62. The treatment tool outlet 80 communicates with the treatment tool inlet 24 (see FIG. 1) of the operation unit 10 through a treatment tool-insertion channel 82 that is inserted into and disposed in the insertion unit 12. Accordingly, in a case where the endoscope is inserted into a body cavity and a treatment or an observation is made, a treatment tool inserted from the treatment tool inlet 24 is led out of the treatment tool outlet 80 (see FIG. 4) to the elevator-housing space 62.

The elevator 60 is disposed at a position in front of the treatment tool outlet 80 of the elevator-housing space 62. The elevator 60 is provided so as to be rotatable about a rotating shaft 92 between a standing position and a fallen position. The elevator 60 is made of a metal material, such as stainless steel, and includes a concave guide surface 60a that is provided on the upper surface thereof and is curved upward toward the distal end side from the proximal end side of the distal-end-part body 36. A treatment tool led out of the treatment tool outlet 80 is led out of the opening portion 58, which is provided on the upper side of the elevator-housing space 62, along the guide surface 60a upward with respect to the direction of the longitudinal axis of the insertion unit 12.

Further, the elevator 60 is adapted to rotate about the rotating shaft 92 and to stand by the operation of the standing operation lever 18 shown in FIG. 1. In a case where the elevator 60 is made to stand so that the standing angle of the elevator 60 from a fallen state is adjusted, the lead-out direction (lead-out angle) of the treatment tool led out of the opening portion 58 can be changed.

The distal-end-part body 36 includes a standing unit 63, and the elevator 60 is disposed in the standing unit 63. The standing unit 63 is made of, for example, a metal material having corrosion resistance.

Since the treatment tool-insertion channel 82 shown in FIG. 4 is also connected to a suction channel (not shown), body fluid and the like can also be sucked from the opening portion 58 in a case where the suction button 22 shown in FIG. 1 is operated.

The observation window 44 is provided on an observation means-forming surface 72a that is provided on the proximal end side of the elevator-housing space 62. An image pickup system unit where an image-forming optical system and a solid image pickup element of an image pickup unit are integrally assembled is housed in the observation window 44. Accordingly, in a case where light, which is emitted from a treatment unit and is in the visual field range of the image pickup unit, enters from the observation window 44, the light forms an observation image on the solid image pickup element through the image-forming optical system. That is, the image of the treatment unit is picked up by the solid image pickup element.

The first illumination window 46A and the second illumination window 46B are provided on illumination means-forming surfaces 72b and 72c. Light emitting parts of an illumination unit are housed in the first illumination window 46A and the second illumination window 46B. Illumination light, which is transmitted through the light guide from the light source device connected to the universal cord 14, is emitted from the light emitting parts, and the treatment unit in the visual field range of the image pickup unit is irradiated with the illumination light through the first illumination window 46A and the second illumination window 46B.

The air/water supply nozzle 48 is provided on a nozzle-forming surface 72d. Then, a washing solution, water, air, or the like is jetted toward the observation window 44 from the air/water supply nozzle 48 shown in FIGS. 2 and 3 by the operation of the air/water supply button 20 shown in FIG. 1, so that the washing of the observation window 44 and the like are performed.

Next, a positional relationship among the opening portion 58, the elevator-housing space 62, and the observation window 44 will be described. As shown in FIG. 2, the position of the observation window 44 in a direction indicated by an arrow A (a direction where the opening portion 58 is opened) is disposed at a position on the side opposite to the elevator-housing space 62 in a case where the position of the opening portion 58 is set as a reference position. That is, in a case where the distal-end-part body 36 is projected onto a virtual plane orthogonal to the direction of the longitudinal axis 38, the observation window 44 is disposed on the opening side (the opening portion 58 side) of the elevator-housing space 62. In a case where the observation window 44 is disposed above the opening portion 58 as described above, a treatment tool can be made to be in the observation visual field of the observation window 44 at a position where the treatment tool is led out of the opening portion 58. Accordingly, since the treatment tool can be guided to the target position, the targeting property of the treatment tool to the target position can be improved.

It is preferable that the positions of the observation window 44 and the elevator-housing space 62 in a direction indicated in FIG. 2 by an arrow B are disposed so that the observation window 44 is offset from the elevator-housing space 62 in the direction indicated by the arrow B. The fact that the observation window 44 is offset from the elevator-housing space 62 in the direction indicated by the arrow B means that the center line of the observation window 44 is shifted from the center line of the elevator 60 in the direction indicated by the arrow B. According to this configuration, it is possible to prevent the observation visual field of the observation window 44 from being obstructed by the treatment tool and the elevator 60 even in a state where the elevator 60 is made to stand and the treatment tool is led out of the opening portion 58. Accordingly, it is possible to reliably check a treatment position through the observation window 44.

The standing unit 63 made of metal is built in a body case 37 made of a resin, so that the distal-end-part body 36 is formed. The elevator-housing space 62 is formed by the elevator-housing space-forming wall 64. A part of the elevator-housing space-forming wall 64 is formed by the standing unit 63, and the other part thereof is formed by the body case 37.

The elevator-housing space-forming wall 64 includes an opening wall portion 66 provided on the opening portion 58 side thereof. Further, the opening wall portion 66 includes an opposite wall portion 66A that is opposite to the guide surface 60a of the elevator 60 in a state where the elevator 60 shown in FIG. 4 by a two-dot chain line is in the standing position. The opposite wall portion 66A is a portion of a component of the standing unit 63. That is, the opposite wall portion 66A is made of metal. Further, the other wall portion 70 of the opening wall portion 66 other than the opposite wall portion 66A is a portion of a component of the body case 37, and is made of a resin.

That is, since the opposite wall portion 66A is made of metal and the other wall portion 70 is made of a resin in this embodiment, the opposite wall portion 66A is made of a material harder than the other wall portion 70. "The other wall portion" means a wall portion provided closer to the distal end side than the elevator 60 and wall portions provided on both sides of the elevator 60, of the opening wall portion 66 forming the opening portion 58.

The standing unit 63 is provided with the treatment tool outlet 80 that is connected to the distal end of the treatment tool-insertion channel 82. Further, the treatment tool outlet 80 is formed by an outlet-forming wall 86. That is, the treatment tool outlet 80 and the outlet-forming wall 86 are formed by the standing unit 63. The opposite wall portion 66A is formed integrally with the outlet-forming wall 86 and is made of the same material as the outlet-forming wall 86.

Furthermore, the opposite wall portion 66A includes a convex portion 68 that protrudes toward the distal end side in the direction of the longitudinal axis 38. The convex portion 68 is formed in a convex shape corresponding to the concave guide surface 60a of the elevator 60. Since the convex shape of the convex portion 68 corresponds to the concave shape of the guide surface 60a, a guide wire can be fixed (a guide wire can be locked) by being sandwiched between the guide surface 60a and the convex portion 68 in a state where the elevator 60 is in the standing position.

Figure 5:
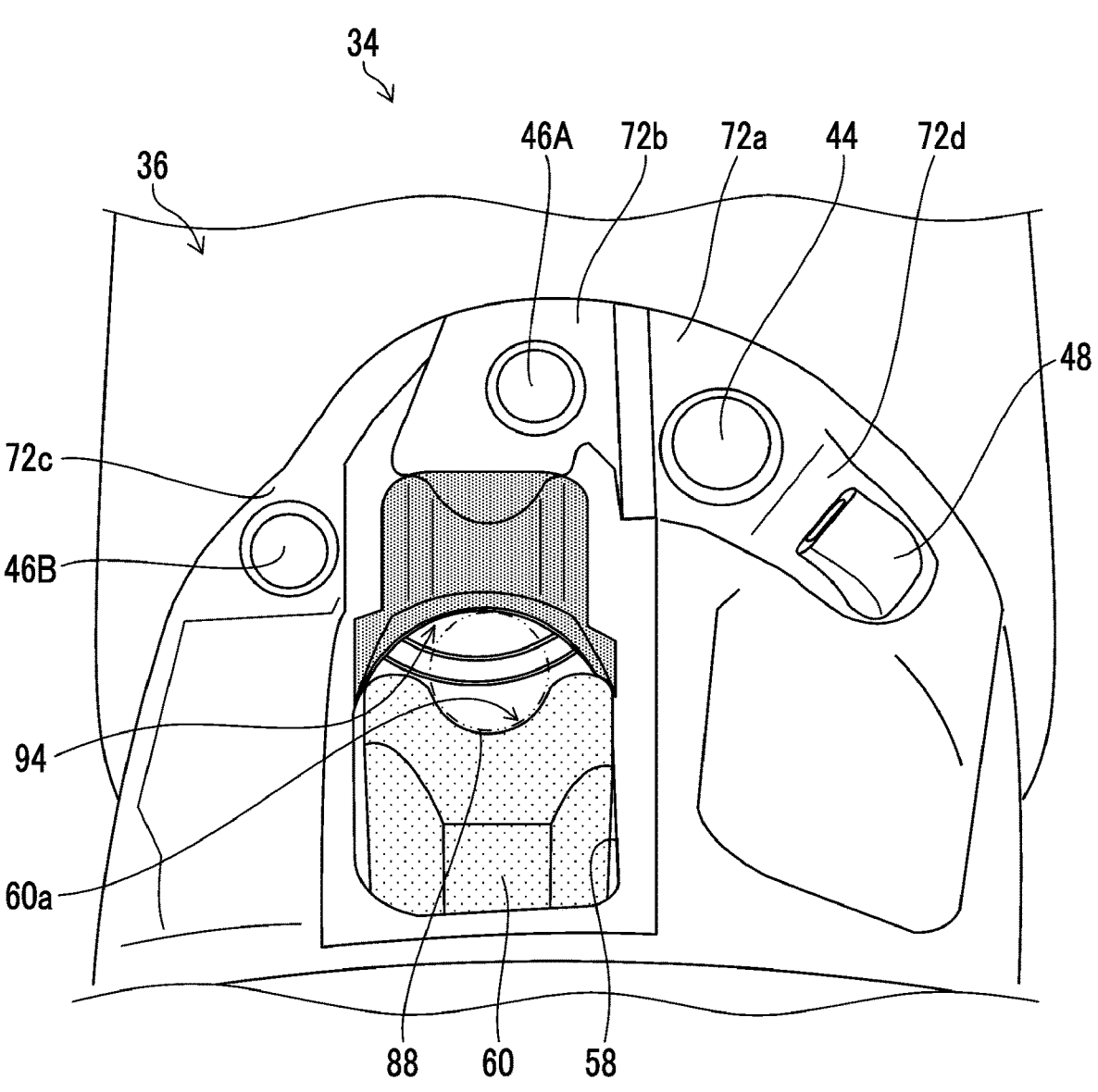
FIG. 5 is a diagram showing a state where the elevator is in a fallen position as seen in a direction C of FIG. 4.
Figure 6:
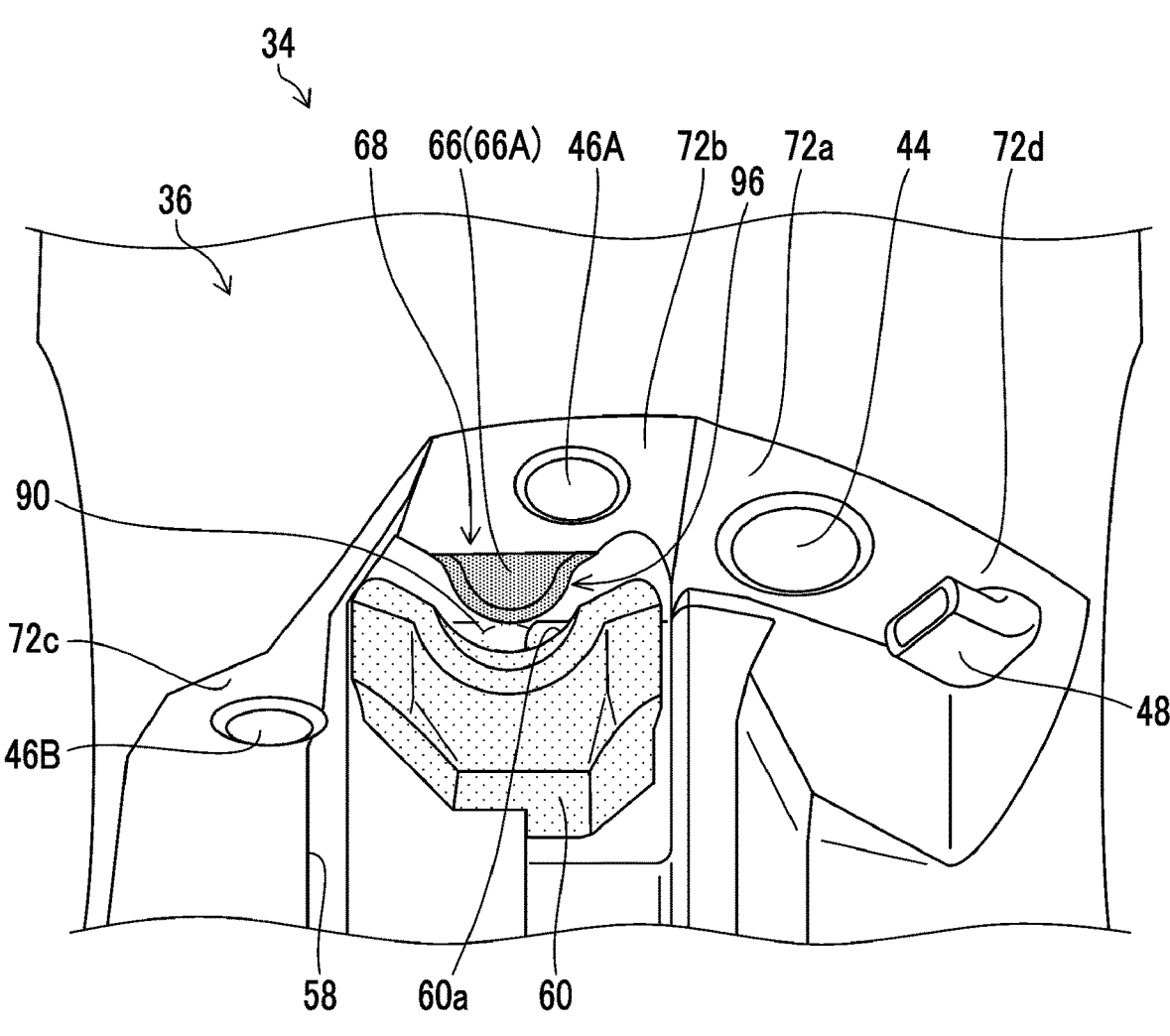
FIG. 6 is a diagram showing a state where the elevator is in a standing position as seen in a direction D of FIG. 4.
Figure 7:
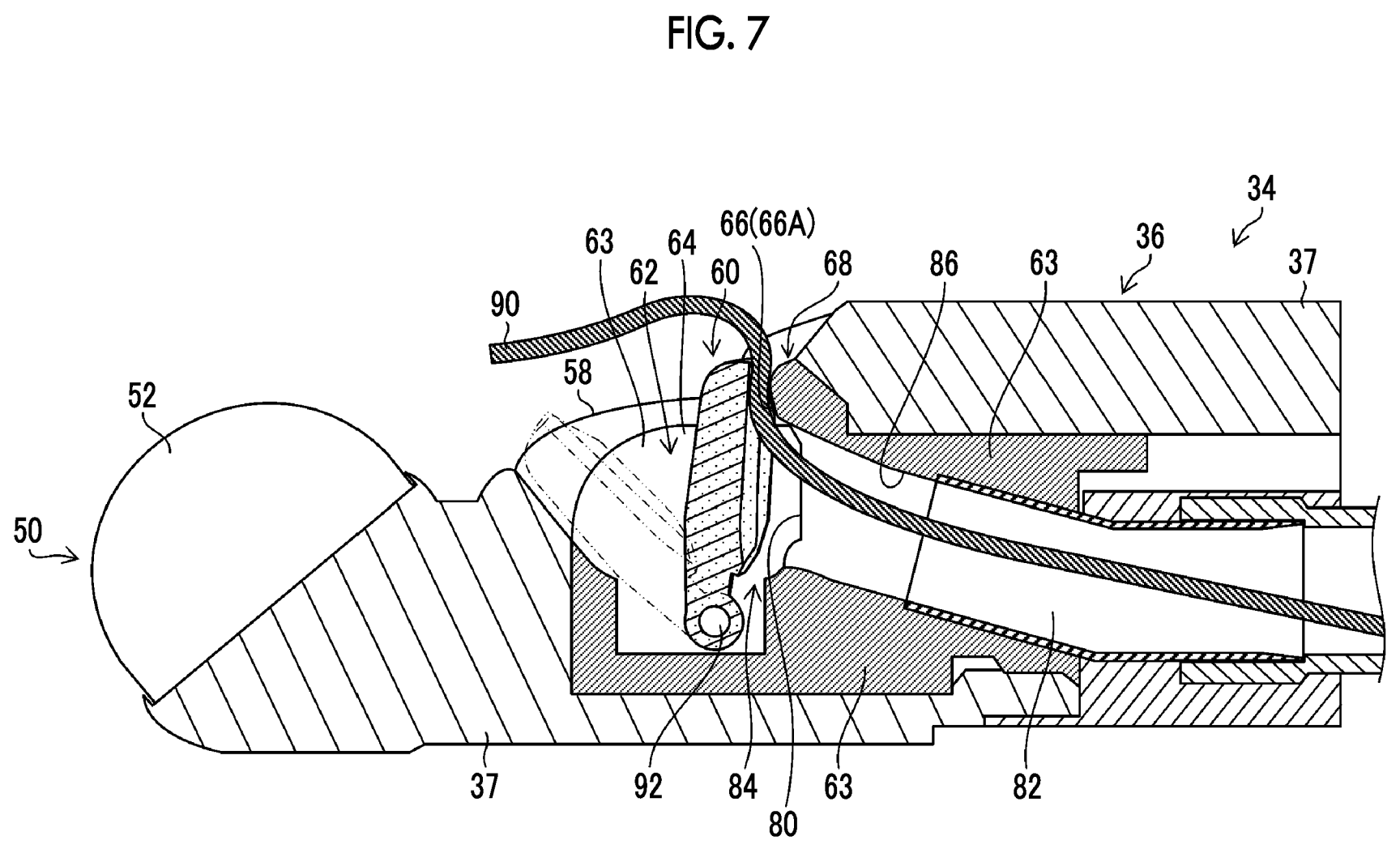

FIGS. 5 to 7 are diagrams showing that a treatment tool is held by the opposite wall portion 66A and the elevator 60, and FIG. 5 is a diagram showing a state where the elevator 60 is in the fallen position as seen in a direction C of FIG. 4. FIG. 6 is a diagram showing a state where the elevator 60 is in the standing position as seen in a direction D of FIG. 4. FIG. 7 is a side cross-sectional view showing a state where a guide wire 90 is fixed by the elevator 60 and the opposite wall portion 66A.

As shown in FIG. 5, the convex portion 68 formed on the opposite wall portion 66A includes a first surface formed on the side thereof facing the elevator-housing space 62, and the first surface 94 is formed in a concave shape so that the first surface 94 and the guide surface 60a of the elevator 60 are apart from each other. Accordingly, for example, a treatment tool having a large diameter like a puncture needle 88 shown in FIG. 5 by a two-dot chain line can be held between the two surfaces (the first surface 94 and the guide surface 60a) that are formed in a concave shape so as to be apart from each other. Therefore, the treatment tool can be stably held without a shift in position in a lateral direction in FIG. 5 (a direction B in FIG. 2).

Further, in a case where the convex portion 68 is formed in a convex shape so as to follow the shape of the concave guide surface 60a and a second surface 96 including an apex of the convex portion 68 and the guide surface 60a approach each other in a state where the elevator 60 is made to further stand than that in FIG. 5 as shown in FIGS. 6 and 7, a treatment tool having a small diameter like a guide wire 90 shown in FIG. 6 by a two-dot chain line can be held. The second surface 96 serves as a contact surface to be in contact with the treatment tool. Since the guide wire 90 has a small diameter and low bending stiffness, the guide wire 90 is bent as shown in FIG. 7 even though the guide wire 90 is sandwiched by the elevator 60 and the convex portion 68. Accordingly, the guide wire can be fixed without being separated from an insertion point where puncture is performed with a puncture needle.

As described above, the guide wire 90 is sandwiched and fixed by the guide surface 60a of the elevator 60 and the convex portion 68 of the opposite wall portion 66A. In a case where the opposite wall portion 66A is made of a material harder than the other wall portion 70 of the opening wall portion 66 other than the opposite wall portion 66A, it is possible to prevent the opposite wall portion 66A from being scraped off due to the standing force of the elevator 60 even though the treatment tool is sandwiched by the guide surface 60a and the convex portion 68 and the opposite wall portion 66A. Further, since the convex portion 68 is provided, the guide wire can be fixed by being sandwiched between the guide surface 60a and the convex portion 68. Ceramic can be used as the material of the opposite wall portion 66A in addition to metal.

Furthermore, it is preferable that a gap between the guide surface 60a and the distal end of the apex of the convex portion 68 is 0.5 mm or less in a state where the elevator 60 is in the standing position. Since the diameter of a general guide wire is 0.6 mm, the guide wire can be sandwiched by the convex portion 68 and the guide surface 60a in a case where the gap is set to 0.5 mm or less.

According to this embodiment, as described above, the opposite wall portion 66A, which is opposite to the guide surface 60a in a case where the elevator 60 is in the standing position, of the opening wall portion 66 provided on the opening side of the elevator-housing space-forming wall 64 forming the elevator-housing space 62 is made of a material harder than the other wall portion 70 other than the opposite wall portion 66A. Accordingly, it is possible to prevent the opposite wall portion from being scraped off in a case where the treatment tool is sandwiched by the guide surface 60a and the opposite wall portion 66A. Further, since the opposite wall portion 66A is made of a hard material, it is possible to prevent the opposite wall portion from being scraped off even though the treatment tool is sandwiched with a large standing force. Furthermore, since the convex portion 68 is provided, the guide wire can be fixed by being sandwiched between the guide surface 60a and the convex portion 68.

Modification Example

Figure 8:
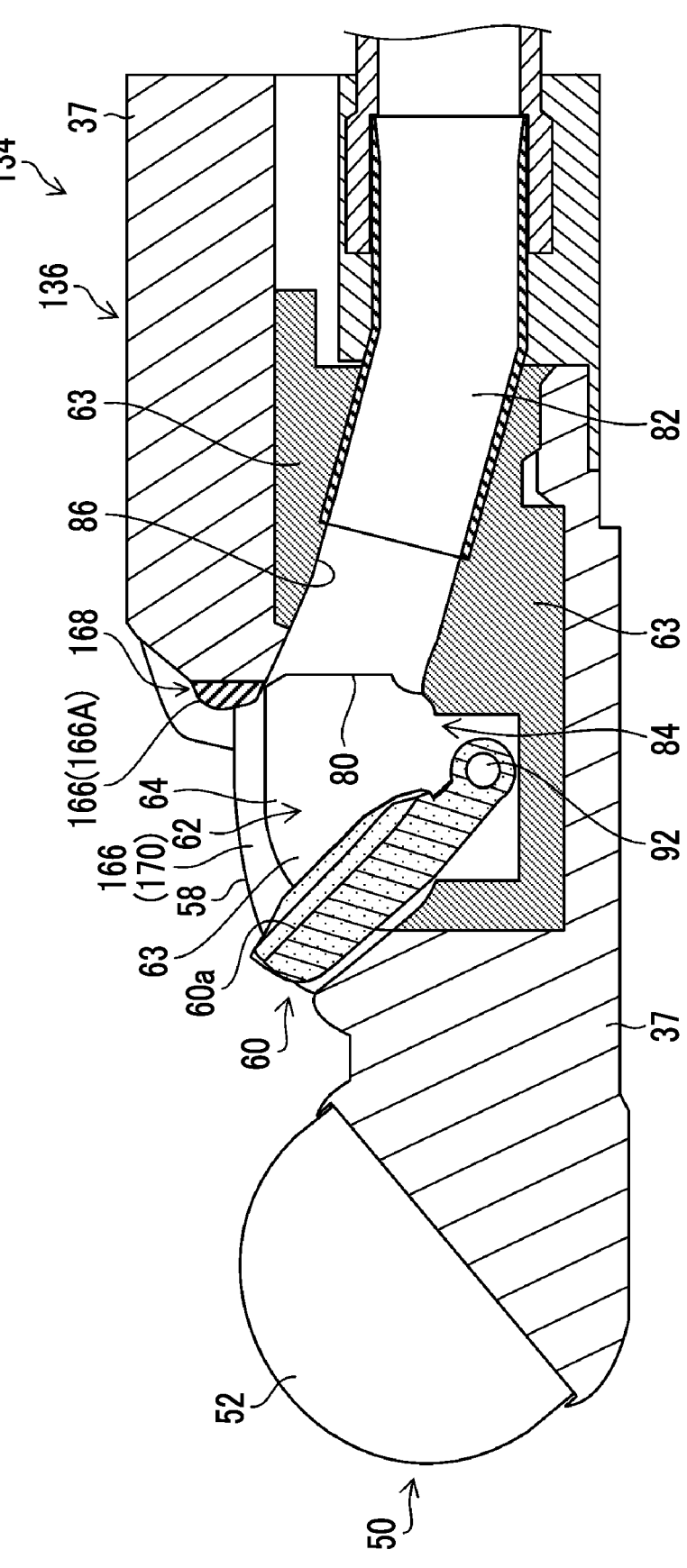
FIG. 8 is a side cross-sectional view showing the configuration of a distal end part of a modification example of a first embodiment.

FIG. 8 is a side cross-sectional view showing the configuration of a distal end part of a modification example of the first embodiment. The opposite wall portion 66A of the distal end part 34 shown in FIGS. 2 to 4 is formed as a portion of a component of the standing unit 63, and is formed integrally with the outlet-forming wall 86.

In contrast, in a distal end part 134 shown in FIG. 8, an opposite wall portion 166A, which includes a convex portion 168 of an opening wall portion 166, is formed separately from the standing unit 63 and is made of a material harder than the other wall portion 170. Even though only the opposite wall portion 166A is made of a hard material as described above, it is possible to prevent the degradation of a distal-end-part body 136 caused by the scrape of the opposite wall portion 166A since only the opposite wall portion 166A is pressed by the elevator 60 in a case where a guide wire is fixed. Further, the material of the opposite wall portion 166A can be changed to a hard material, separately from the standing unit 63.

Second Embodiment

Figure 9:
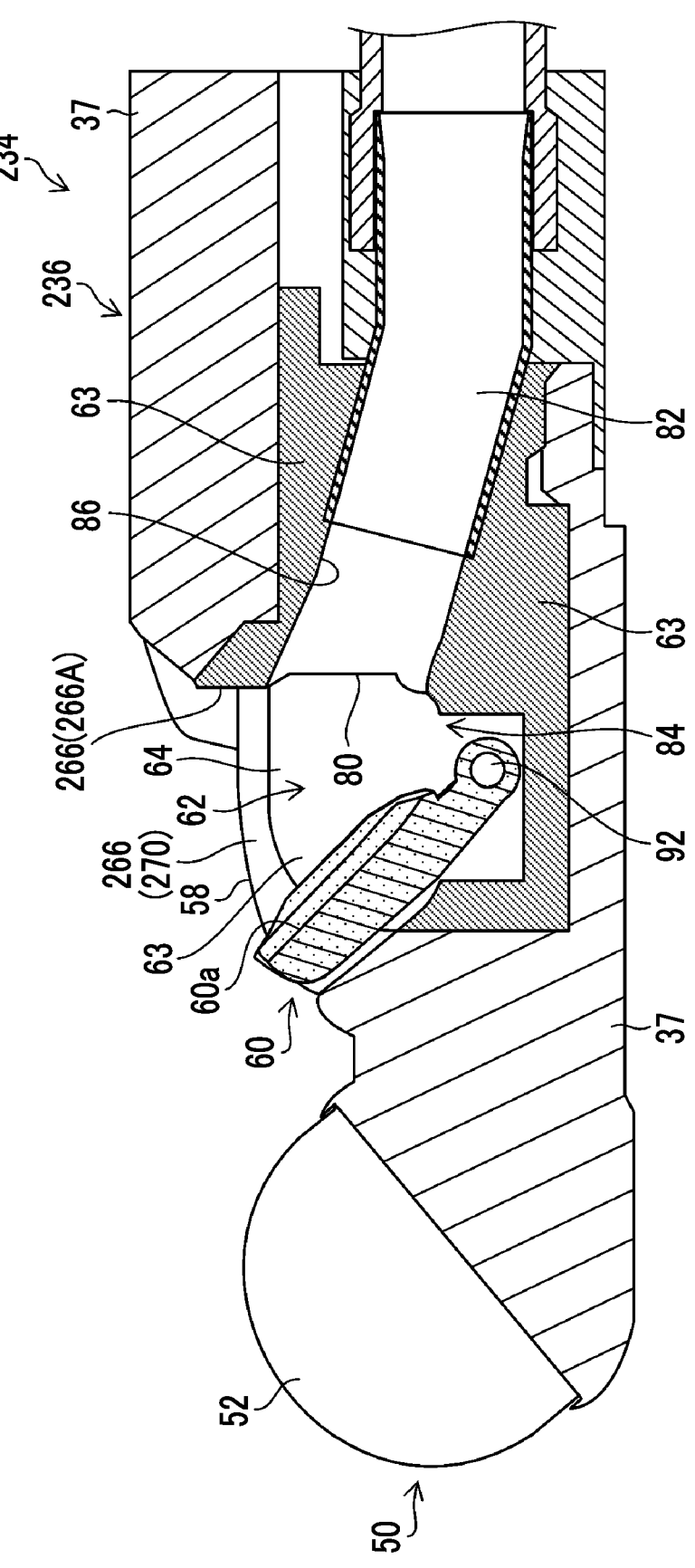
FIG. 9 is a side cross-sectional view showing the configuration of a distal end part of a second embodiment.

FIG. 9 is a side cross-sectional view showing the configuration of a distal end part 234 of an endoscope according to a second embodiment. The distal end part 234 of the second embodiment is different from the distal end part 34 of the endoscope according to the first embodiment in that a convex portion is not provided on an opposite wall portion 266A of an opening wall portion 266. Even in the second embodiment, the opposite wall portion 266A is made of a material harder than the other wall portion 270.

Even though the convex portion is not provided, a treatment tool having a large diameter can be sandwiched by the opposite wall portion 266A and the elevator 60. In a case where the opposite wall portion 266A is made of a hard material at this time, it is possible to prevent the opposite wall portion 266A from being scraped off even though a treatment tool is pressed against the opposite wall portion 266A by the elevator 60. Accordingly, the degradation of the distal-end-part body 236 over time can be prevented.

The convex ultrasound transducer has been described above, but the invention is not limited to the convex ultrasound transducer and can also be applied to a radial ultrasound transducer.

EXPLANATION OF REFERENCES

1: endoscope
10: operation unit
12: insertion unit
14: universal cord
16: angle knob
18: standing operation lever
20: air/water supply button
22: suction button
24: treatment tool inlet
30: soft part
32: bendable part
34, 134, 234: distal end part
36, 136, 236: distal-end-part body
37: body case
38: longitudinal axis of insertion unit
40: base portion
42: extension portion
44: observation window
46A: first illumination window
46B: second illumination window
48: air/water supply nozzle
50: ultrasound transducer
52: ultrasound transmitting/receiving surface
58: opening portion

60: elevator
60a: guide surface
62: elevator-housing space
63: standing unit
64: elevator-housing space-forming wall
66, 166, 266: opening wall portion
66A, 166A, 266A: opposite wall portion
68, 168: convex portion
70, 170, 270: other wall portion
72a: observation means-forming surface
72b, 72c: illumination means-forming surface
72d: nozzle-forming surface
80: treatment tool outlet
82: treatment tool-insertion channel
84: lead-out portion
86: outlet-forming wall
88: puncture needle
90: guide wire
92: rotating shaft
94: first surface
96: second surface

What is claimed is:

1. An endoscope comprising:
an insertion unit that has a soft part, a bendable part, and a distal end part arranged in order from a proximal end side toward a distal end side in a direction of a longitudinal axis;
a treatment tool insertion channel that is inserted into the insertion unit;
a treatment tool outlet that is connected to a distal end of the treatment tool insertion channel;
an elevator that is rotatable about a rotating shaft between a standing position and a fallen position and includes a guide surface guiding a treatment tool led out of the treatment tool outlet;
a plurality of walls that encloses a space in which the elevator is housed, wherein a first wall, which is opposite to the guide surface in a case where the elevator is in the standing position, among the plurality of walls is made of a material harder than at least a second wall among the plurality of walls; and
a resin body case built-in with a standing unit, in which the elevator is disposed and the treatment tool outlet is provided,
wherein the first wall includes a first contact surface that is to be in contact with the treatment tool led out of the treatment tool outlet in a case where the elevator is in the standing position, and the standing unit includes a second contact surface that faces oppositely to the first contact surface and is to be in contact with the elevator in a case where the elevator is in the fallen position.

2. The endoscope according to claim 1,
wherein the second wall is opposite to the first wall, and the first wall is disposed closer to the proximal end side in the direction of the longitudinal axis than the second wall and is made of a material harder than the second wall.

3. The endoscope according to claim 2,
wherein the second wall constitutes a part of the resin body case.

4. The endoscope according to claim 1,
wherein the second wall is one of a plurality of side walls extending along the direction of the longitudinal axis among the plurality of walls.

5. The endoscope according to claim 4,
wherein the side walls constitute parts of the resin body case.

6. The endoscope according to claim 1,
wherein the standing unit and the first wall are formed integrally.

7. The endoscope according to claim 6,
wherein the elevator is made of metal.

8. The endoscope according to claim 1,
wherein the standing unit and the first wall are formed separately.

9. The endoscope according to claim 1,
wherein the first wall is made of metal or ceramic.

10. The endoscope according to claim 1,
wherein the first wall includes a convex portion that has a convex shape and protrudes toward the distal end side in the direction of the longitudinal axis, and
the first contact surface is formed of a surface including an apex of the convex portion.

11. The endoscope according to claim 10,
wherein the guide surface that has a concave shape corresponding to a shape of the convex portion.

12. The endoscope according to claim 11,
wherein a gap between the guide surface and the convex portion is 0.5 mm or less in a state where the elevator is in the standing position.

13. The endoscope according to claim 1, further comprising:
an ultrasound transducer including ultrasound vibrators,
wherein the elevator is disposed closer to the proximal end side in the direction of the longitudinal axis than the ultrasound transducer.

14. The endoscope according to claim 13, further comprising:
an observation window disposed on the proximal end side of the ultrasound transducer in the direction of the longitudinal axis.

15. The endoscope according to claim 14,
wherein the observation window is disposed closer to the proximal end side in the direction of the longitudinal axis than the first wall.

16. The endoscope according to claim 14,
wherein the observation window is offset from the standing unit in a direction away from a center line of the elevator and toward a lateral side of the distal end part.

17. The endoscope according to claim 1,
wherein the resin body case forms an outer wall of the distal end part and houses the elevator, and the first wall is built-in the resin body case and is made of ceramic.

* * * * *